United States Patent [19]

Main

[11] Patent Number: 5,229,414
[45] Date of Patent: Jul. 20, 1993

[54] DIAMINE COMPOUNDS

[75] Inventor: Brian G. Main, Sandbach, England

[73] Assignee: Imperial Chemical Industries PLC, London, England

[21] Appl. No.: 697,484

[22] Filed: May 2, 1991

Related U.S. Application Data

[63] Continuation of Ser. No. 298,972, Jan. 19, 1989, abandoned.

[30] Foreign Application Priority Data

Jan. 21, 1988 [GB] United Kingdom ............... 8801304

[51] Int. Cl.$^5$ ............... A61K 31/40; C07D 295/073; C07D 295/104
[52] U.S. Cl. ............... 514/428; 548/567; 548/568
[58] Field of Search ............... 548/568, 567, 565; 514/428, 331; 546/230, 231, 232

[56] References Cited

U.S. PATENT DOCUMENTS

| | | | |
|---|---|---|---|
| 2,576,106 | 11/1951 | Cusic | 548/568 X |
| 2,580,411 | 1/1952 | Cusic | 548/568 X |
| 2,850,498 | 9/1958 | Pohland | 260/294 |
| 3,103,516 | 9/1963 | Schmitt et al. | 548/568 X |
| 3,145,209 | 8/1964 | Krapcho | 260/268 |
| 3,366,674 | 1/1968 | Geiger | 260/501.17 |
| 3,502,652 | 3/1970 | Tucker et al. | 548/567 X |
| 4,145,435 | 3/1979 | Szmuszkovicz | 546/238 X |
| 4,499,286 | 2/1985 | Binder | 546/213 X |
| 4,504,663 | 3/1985 | Moinet et al. | 546/144 |

FOREIGN PATENT DOCUMENTS

| | | |
|---|---|---|
| 0126612 | 11/1984 | European Pat. Off. |
| 0254545 | 1/1988 | European Pat. Off. |
| 0261842 | 3/1988 | European Pat. Off. |

OTHER PUBLICATIONS

Chiti et al., Farmaco, vol. 12, No. 7, (1957), pp. 551–575.
Costello, et al., Eur. J. Pharm. 151 (1988), pp. 475–478.
Shawn, et al., Br. J. Pharm., 96 (1989), pp. 986–992.
Cromwell, N. H., et al., J.A.C.S. 66, (1944), pp. 870–871.

*Primary Examiner*—Joseph Paul Brust
*Attorney, Agent, or Firm*—Cushman, Darby & Cushman

[57] ABSTRACT

Compounds of the general formula I $$R^1-X-\overset{O}{\overset{\|}{C}}-\underset{R^2}{\overset{H}{\overset{|}{N}}}-\overset{R^3}{\overset{|}{C}}-CH_2-N\overset{R^4}{\underset{R^5}{\diagdown}}$$

wherein
  $R^1$ represents a halophenyl, dihalophenyl, nitrophenyl, cyanophenyl or trifluoromethylphenyl group;
  X represents a single bond, $-CH_2-$, $-OCH_2-$, $SCH_2$, $-S(O)-CH_2-$, $-S(O)_2-CH_2-$ or $-CH_2CH_2-$
  $R^2$ represents hydrogen or $C_{1-3}$ alkyl;
  $R^3$ represents a phenyl group substituted in the meta-position by a radical containing an organic base, an organic acid or a quaternary ammonium salt and optionally further substituted.
  $R^4$ and $R^5$ which may be the same or different each represents a $C_{3-5}$ alkenyl, $C_{3-5}$alkynyl, $C_{1-6}$alkyl, or $C_{4-7}$cycloalkylalkyl group, or together with the intervening nitrogen atom represents a 4–7 membered heterocyclic ring, and the pharmaceutically acceptable salts thereof are useful for the treatment of hypertension and/or inflammation in the warm-blooded animals.

Also disclosed are processes for their preparation and pharmaceutical compositions containing them.

10 Claims, 2 Drawing Sheets

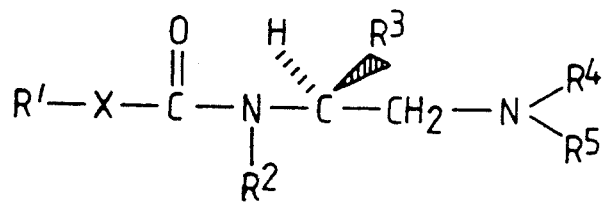 I
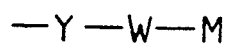 II
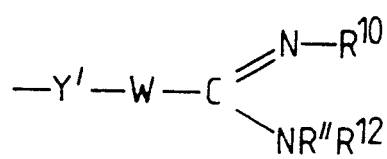 III
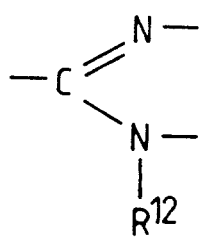 IV
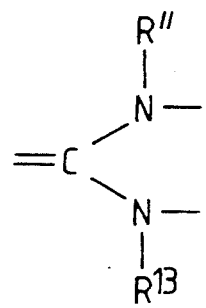 IVa
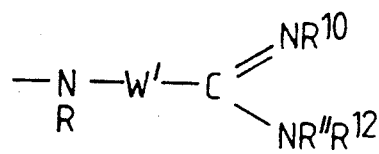 V
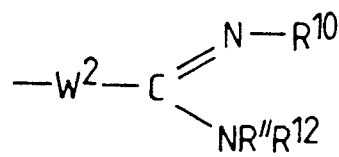 VI
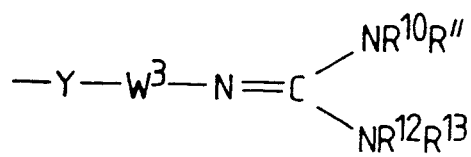 VII
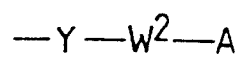 VIII

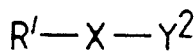 IX
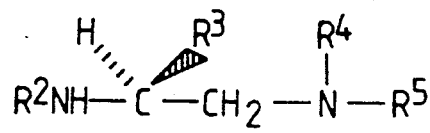 X
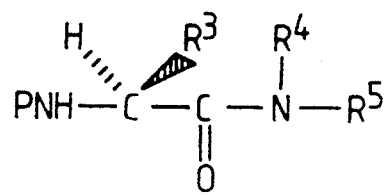 XI
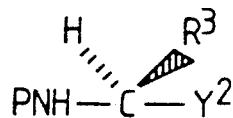 XII
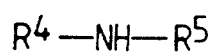 XIII
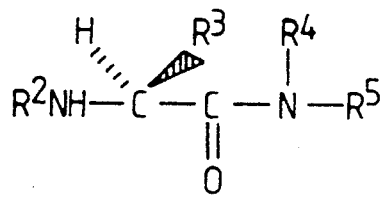 XIV
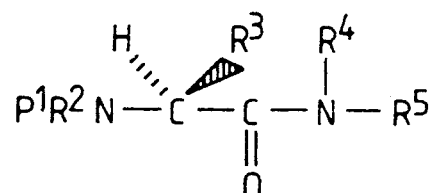 XV
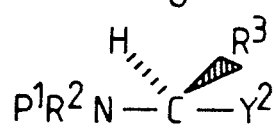 XVI
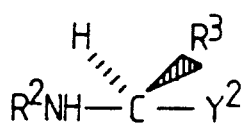 XVII

DIAMINE COMPOUNDS

This application is a continuation of Ser. No. 07/298,972, filed Jan. 19, 1989, now abandoned.

The present invention relates to 1,2-ethylene diamine compounds and the salts thereof, processes for their preparation and pharmaceutical compositions containing the said compounds and the pharmaceutically acceptable salts thereof. The compounds and their pharmaceutically acceptable salts possess a selective effect on peripheral kappa opiate receptors.

U.S. Pat. No. 4,145,435 discloses cis- and trans-N-(2-aminocycloaliphatic)-2-arylacetamide derivatives as possessing potent analgesic activity. European Patent Publication No. 110 869 discloses trans-N-(2-aminocyclohexyl)-2-thienylacetamide derivatives and European Patent Publication No. 126,612 discloses cis- and trans-N-[2-(2,5-dihydro-1-H-pyrrol-1-yl)cycloaliphatic]-2-benzeneacetamide derivatives all possessing analgesic activity.

Our copending European Patent Application No. 87306463.8 describes and claims certain open chain ethylene diamine compounds which possess a significantly improved analgesic potency over corresponding known compounds. The invention in our aforementioned copending European Patent Application is based on the discovery that the cycloaliphatic ring present in the above-mentioned compounds is not essential for activity, and further on the discovery that provided the sterochemical centre is maintained at the carbon adjacent to the amidic nitrogen atom, the open chain ethylene diamine structure enables a wide range of substituents to be introduced which would not otherwise have been possible, whereby compounds having a significantly improved analgesic potency over corresponding known compounds may be obtained.

The present invention is based on the discovery that compounds possessing a selective effect on peripheral kappa receptors are obtained if a phenyl group substituted in the meta-position by a radical comprising an organic base, an organic acid or a quaternary ammonium salt (and optionally further substituted), is present on the carbon adjacent to the amidic nitrogen atom of the aforementioned open chain ethylene diamine compounds, the metal-substituent being selected such that the compounds of the invention have a log D of less than 0.5 at pH 7.4 (where log D is the logarithm of the distribution coefficient between octan-1-ol and aqueous buffer). The side-effects associated with centrally acting kappa agonists such as dysphoria and other CNS problems are thus significantly amelioriated in the compounds of the present invention.

BRIEF DESCRIPTION OF THE DRAWINGS

FIG. 1 shows the formulas reference below and designated I to XVII.

According to one feature of the present invention there are provided compounds of formula I (as set out hereinafter) wherein $R^1$ represents a halophenyl, dihalophenyl, nitrophenyl, cyanophenyl or trifluoromethylphenyl group;

X represents a single bond, —$CH_2$—, $OCH_2$—, —$SCH_2$—, —$S(O)$—$CH_2$—, —$S(O)_2$—$CH_2$— or —$CH_2$—$CH_2$—;

$R^2$ represents hydrogen or $C_{1-3}$ alkyl;

$R^3$ represents a phenyl group substituted in the metal position by a radical containing an organic base, an organic acid or a quaternary ammonium salt and optionally further substituted by halogen, $C_{1-3}$alkyl, $C_{1-3}$alkoxy, cyano, nitro, hydroxy, amino, mono- or di-($C_1$ or $_2$alkyl)amino, carboxamido, mono- or di-($C_1$ or $_2$alkyl)carboxamido, uriedo or $C_{1-3}$acylamino;

$R^4$ and $R^5$, which may be the same or different, each represents a $C_{3-5}$ alkyenyl, $C_{3-5}$ alkynyl, $C_{1-6}$ alkyl, or $C_{4-7}$ cycloalkylalkyl group;

or $R^4$ and $R^5$ together with the intervening nitrogen atom represent a 4-7-membered heterocyclic ring which optionally contains a further heteroatom selected from oxygen and sulphur or racemates thereof, and the salts of said compounds or racemates; the group —$R^3$ being selected such that the compound of formula I or racemate thereof or salt of said compound of formula I or racemate thereof has a log D of less than 0.5 at pH 7.4 (where log D is the logarithm of the distribution coefficient between octan-1-ol and aqueous buffer).

Unless otherwise specified, reference herein to alkyl, alkenyl and alkynyl groups include such groups in both straight chain and branched forms.

The compounds of formula I possess an asymmetric carbon atom, that being the carbon atoms carrying the $R^3$ substituent in formula I. It will be understood that the present invention includes the racemates of the compounds of formula I as well as the optionally active enantiomer having the absolute configuration at the above-mentioned asymmetric carbon atom which would be obtained by synthesis from a corresponding natural (L)-alpha-amino acid as indicated in formula I which compounds possess the useful physiological properties of the compounds of the invention herein described.

Furthermore the substituent $R^3$ may contain at least one asymmetric carbon atom and it will be understood that the present invention encompasses the racemic form of such compounds as well as any individual optical isomers thereof which possess the useful physiological properties of the compounds of the present invention as herein defined, it being common general knowledge to those skilled in the art how such isomers may be separated and how their physiological properties may be determined.

The present invention encompasses the salts of the compounds of formula I or racemate thereof. It will be appreciated, however, that for pharmaceutical use, the salts referred to will be pharmaceutically acceptable, but other salts may find use, for example in the preparation of compounds of formula I and their pharmaceutically acceptable salts. The salts of the present invention include acid addition salts with for example mineral acids such as hydrochloric acid and organic acids such as maleic and fumaric acid.

The compounds of the present invention, have a log D of less than 0.5 at pH 7.4. The distribution coefficient (D) between octan-1-ol and aqueous buffer at pH 7.4 of a compound of the present invention may be determined as described hereinafter.

Where $R^4$ and $R^5$ together with the intervening nitrogen atom represent a 4-7 membered ring optionally containing a further heteroatom, particular values for said ring are the pyrrolidinyl, pyrrolinyl, morpholinyl or piperidinyl group.

Particular values for $R^1$ are chlorophenyl such as 3-chlorophenyl or 4-chlorophenyl; dichlorophenyl such as 3,4-dichlorophenyl; bromophenyl such as 4- bromophenyl; or fluorophenyl such as 3-fluorophenyl or 4-fluorophenyl; difluorophenyl such as 3,4-difluorophenyl; trifluoromethylphenyl such as 4-(trifluoromethyl)phenyl; nitrophenyl such as 4-nitrophenyl; and cyanophenyl such as 4-cyanophenyl.

Particular values for X are $-CH_2-$, $-OCH_2$, $-SCH_2-$ or $-CH_2-CH_2-$, especially $-CH_2-$.

Particular values for $R^2$ are hydrogen, methyl, ethyl or isopropyl, especially methyl.

Particular values for $R^3$ are phenyl substituted in the meta-position by:

(i) a group of the formula;

$$-Y-W-M \qquad II$$

in which Y represents a single bond, $-S-$, $-O-$ or $-NR-$ (in which R represents hydrogen, methyl, formyl or acetyl), W represents a $C_{2-4}$alkylene chain which may if desired be branched and M represents the group $-NR^7R^8R^9$ (wherein $R^7$, $R^8$ and $R^9$, which may be the same or different, each represents a $C_{1-7}$alkyl or aralkyl group;

(ii) a group of the formula III in which $Y^1$ represents $-O-$ or $-S-$; W represents a $C_{2-4}$alkylene chain which may if desired be branched; and $R^{10}$, $R^{11}$ and $R^{12}$, which may be the same or different, each represents hydrogen or methyl or $R^{10}$ and $R^{11}$ together represent a $C_2$ or $_3$ alkylene chain such that $R^{10}$ and $R^{11}$ together with the intervening radical of formula IV form a 4,5-dihydroimidazol-2-yl or 3,4,5,6-tetrahydropyrimidin-2-yl ring, $R^{12}$ representing hydrogen or methyl; or $R^{11}$ and $R^{12}$ together represent a $C_4$ or $_5$ alkylene chain such that $R^{11}$ and $R^{12}$ together with the intervening nitrogen atom form a pyrrolidine or piperidine ring and $R^{10}$ represents hydrogen or methyl;

(iii) a group of the formula V in which $W^1$ represents a $C_{2-4}$alkylene chain which may if desired be branched and $R^{10}$, $R^{11}$ and $R^{12}$ are as hereinbefore defined.

(iv) a group of the formula VI in which $W^2$ represents a $C_{1-4}$alkylene chain which may if desired be branched and $R^{10}$, $R^{11}$ and $R^{12}$ are as hereinbefore defined;

(v) a group of the formula VII in which Y is as hereinbefore defined, $W^3$ represents a $C_{2-4}$alkylene chain which may if desired be branched or where Y represents a single bond $W^3$ may represent a single bond or a $C_{1-4}$alkylene chain which may if desired be branched and $R^{10}$, $R^{11}$, $R^{12}$ and $R^{13}$, which may be the same different, each represents hydrogen or methyl, or $R^{10}$ and $R^{12}$ together represent a $C_2$ or $_3$ alkylene chain such that $R^{10}$ and $R^{12}$ together with the intervening radical of formula IVa form a 4,5-dihydroimidazol-2-yl or 3,4,5,6-tetrahydropyrimidin-2-yl ring or tautomer thereof, $R^{11}$ and $R^{12}$ being independently selected from hydrogen or methyl, or either $R^{10}$ and $R^{11}$ together or $R^{12}$ and $R^{13}$ together represent a $C_4$ or $_5$ alkylene chain such that either $R^{10}$ and $R^{11}$ together with the intervening nitrogen atom form a pyrrolidine or piperidine ring or tautomer thereof and $R^{12}$ and $R^{13}$ are independently selected from hydrogen and methyl or $R^{12}$ and $R^{13}$ together with the intervening nitrogen atom form a pyrrolidine or piperidine ring or tautomer thereof and $R^{10}$ and $R^{11}$ are independently selected from hydrogen and methyl; or (vi) a group of the formula VIII in which Y and $W^2$ are as hereinbefore defined and A represents a carboxylic or sulphonic acid.

Where $R^3$ represents a phenyl group carrying further substituents in addition to the substituent at the meta-position, such further substituents are particularly selected from chlorine, fluorine, methyl, methoxy, cyano, nitro, hydroxy, amino, monomethylamino, dimethylamino, carboxamido, monomethylcarboxamido, dimethylcarboxamido, ureido and acetylamino. However $R^3$ especially represents a phenyl group which is unsubstituted apart from carrying a substituent at the meta-position as herein defined.

$R^3$ is preferably selected such that the organic base, the organic acid or the quaternary ammonium salt is linked to phenyl at the meta position via oxygen or $-NH-$.

Particular values for $R^4$ and $R^5$, which may be the same or different, are each a $C_{1-6}$ alkyl group or a $C_{3-5}$ alkenyl group. Particular values for $R^4$ and $R^5$ together with the intervening nitrogen atom are 5- or 6-membered heterocyclic rings, especially where the nitrogen atom is the sole heteroatom.

More particular values for $R^1$ are 3,4-dichlorophenyl and 4-trifluoromethylphenyl, especially 3,4-dichlorophenyl.

A more particular value for $R^2$ is methyl.

More particular values for $R^3$ are phenyl substituted in the meta-position by:

i) a group of the formula II in which W is $C_2$ or $_3$ alkylene;

ii) a group of the formula III in which W is $CH_2CH_2$;

iii) a group of the formula V in which W is a single bond or $-CH_2CH_2-$;

iv) a group of the formula VI in which W is $-CH_2-$ or $-CH_2CH_2-$;

v) a group of the formula VII in which Y represents $-O-$, $-S-$ or $-NR-$ (wherein R is as hereinbefore defined) and W is $-CH_2CH_2-$; or a group of formula VII in which Y represents a single bond and W is a single bond $-CH_2-$ or $CH_2CH_2-$;

vi) A group of formula VIII in which W is $-CH_2-$;

Where the grouping $>N-R$ is present, as in formulae II, VII or VIII in which Y may represent $>N-R$ or in formulae V or VIII, R is particularly hydrogen.

Where the groupings $R^7$, $R^8$ and $R^9$ are present, such groupings, which may be the same or different, are particularly selected from methyl and benzyl.

Thus $R^3$ may especially represent 3-(3-dimethylaminopropoxy)phenyl in the form of a quaternary ammonium salt and 3-(3-carboxymethoxy)phenyl and 3-guanidinophenyl. Thus $R^3$ may especially represent the 3-trimethylammoniumpropoxy and 3-benzyldimethylammoniumpropoxy groups stabilised by an appropriate anion such as iodide or chloride.

More particular values for $R^4$ and $R^5$ together with the intervening nitrogen atom are pyrrolidino, dimethylamino, diethylamino, N-allyl-N-methylamino, N-isopropyl-N-methylamino, $\Delta^3$-pyrrolino or piperidino, especially pyrrolidino.

Preferred compounds of the present invention, by virtue of their selective effect on peripheral kappa receptors include the following:

2(R,S)-N-[2-(N-methyl-3,4-dichlorophenylacetamido)-2-(3-carboxymethoxyphenyl)-ethyl]pyrrolidine, (R,S)-N-[2-(N-methyl-3,4-dichlorophenylacetamido)-2-(3-trimethylammoniumpropoxyphenyl)-ethyl]-pyrrolidine iodide, (R,S)-N-[2-(N-methyl-3,4-dichlorophenylacetamido)-2-(3-benzyldimehtylammoniumpropoxyphenyl)-ethyl]-pyrrolidine chloride;

(R,S)-N-[2-(N-methyl-3,4-dichlorophenylacetamido)-2-(3-guanidinophenyl)ethyl]pyrrolidine and the salts thereof, especially the pharmaceutically acceptable salts thereof.

Particular sub-groups of the compounds of the present invention of interest may be obtained by taking any one of the above-mentioned particular generic definitions for R, $R^1$, $R^2$, $R^3$, $R^4$, $R^5$, $R^7$, $R^8$, $R^9$, $R^{10}$, $R^{11}$, $R^{12}$, M, W, $W^1$, $W^2$, $W^3$, X, Y or $Y^1$ either singly or in combination with any other particular generic definition(s) for R, $R^1$, $R^2$, $R^3$, $R^4$, $R^5$, $R^7$, $R^8$, $R^9$, $R^{10}$, $R^{11}$, $R^{12}$, M, W, $W^1$, $W^2$, $W^3$, X, Y or $Y^1$.

According to a further feature of the present invention there is provided a process for the preparation of a compound of the invention wherein $R^3$ is as hereinbefore defined with the proviso that the radical comprising an organic base, an organic acid or a quaternary ammonium salt is bonded to phenyl via oxygen or sulphur which process comprises reacting a compound corresponding to a compound of formula I but in which $R^3$ represents a meta hydroxyphenyl or mercaptophenyl group optionally further substituted as hereinbefore defined or a racemate thereof with a compound of the formula $R^6Z$ in which Z represents a leaving atom or group and $R^6$ represents a moiety containing an organic base, an organic acid or a quaternary ammonium salt, $R^6$ optionally being in protected form; whereafter (i) any protecting group present is removed to form a compound of the invention; and/or (ii) where a compound of formula I or a racemate thereof is obtained in the form of a base or acid and a salt is required, reacting said compound of formula I or racemate thereof with respectively an acid or base to form a salt.

The reaction may for example be effected in the presence of a polar solvent, for example a polar aprotic solvent such as dimethylformamide. The reaction is also conveniently effected in the presence of an acid binding agent such as an alkali metal or alkaline earth metal carbonate or bicarbonate such as potassium, sodium or magnesium carbonate. The reaction may for example be effected at a temperature from 10° C. to the boiling temperature of the reaction mixture such as ambient temperature.

According to a further feature of the present invention there is provided a process for the preparation of a compound of the invention wherein $R^3$ is as hereinbefore defined with the proviso that the substituent in the meta-position comprises a quaternary ammonium salt and is bonded to phenyl via oxygen, —NH— or sulphur, which process comprises quaternising a compound which corresponds to a compound of formula I but in which $R^3$ represents a group containing a tertiary amine.

The quaternisation may conveniently be effected in the presence of an alkyl or aralkyl halide such as chloride, bromide or iodide for example iodomethane or benzyl chloride and advantageously in the presence of a solvent inert under the reaction conditions. The quaternisation is also conveniently effected at a temperature of from 10° C. to the reflux temperature of the reaction mixture, preferably at about ambient temperature. The quaternisation may for example be effected in the presence of a polar aprotic solvent such as acetone.

According to a further feature of the present invention there is provided a process for the preparation of a compound of the invention wherein $R^3$ is as hereinbefore defined with the proviso that the substituent in the metal-position is bonded to phenyl via —NH—, which process comprises reacting a compound corresponding to a compound of the formula I but in which $R^3$ represents a meta-aminophenyl group (optionally further substituted as hereinbefore defined) or racemate thereof with a compound of the formula $R^6Z$ (wherein $R^6$ is as hereinbefore defined and Z represents a leaving atom or group or a cyano group), $R^6$ optionally being in protected form; whereafter (i) any protecting group present is removed to form a compound of the invention; and/or (ii) where a compound of formula I or a racemate thereof is obtained in the form of a base or acid and a salt is required, reacting said compound of formula I or racemate thereof with respectively an acid or base to form a salt.

The reaction is conveniently effected at a temperature of from 0° C. to the boiling temperature of the reaction mixture, preferably at a temperature of from 0° C. to 25° C. The reaction may for example be effected in the presence of a polar solvent such as a $C_{1-4}$ alkanol e.g. ethanol.

According to a further feature of the present invention there is provided a process for preparing a compound of the invention, which comprises reacting a compound of formula IX (as set out hereinafter in which $R^1$ and X are as hereinbefore defined and $Y^2$ represents an acid or an activated derivative thereof) with a compound of formula X (as set out hereinafter in which $R^2$, $R^3$, $R^4$ and $R^5$ are as hereinbefore defined) or a racemate thereof, optionally in protected form, and where necessary deprotecting the compound thus obtained to form a compound of formula I or racemate thereof and if desired reacting said compound or racemate with an acid to form a salt.

Such a process may be employed to prepare the compounds corresponding to compounds of formula I but in which $R^3$ represents a metal-hydroxyphenyl or meta-aminophenyl group, such phenyl group being optionally further substituted as hereinbefore defined.

A compound of formula IX may for example be used in which $Y^2$ represents an ester or an acid halide such as an acid chloride, acid anhydride or acyl imidazole.

Where the compound of formula IX used is an ester the reaction may advantageously be effected in the presence of an aprotic solvent or in the absence of a solvent. Such a reaction is preferably effected at a temperature of from ambient to the reflux temperature of the reaction mixture, but where no solvent is employed the reaction is preferably effected at a temperature no greater than 150° C.

Where the compound of formula IX used is an acid chloride, an acid anhydride or an acyl imidazole the reaction is advantageously effected in the presence of an aprotic solvent, preferably at a temperature of from 0°-60° C.

The compound of formula X may be for example be prepared by reaction of a compound of formula XI (wherein P represents a hydrogen atom or an amine protecting group and $R^4$ and $R^5$ are as hereinbefore defined) to convert said compound into a compound of formula X.

Such conversion may be effected in a number of different ways. Thus for example a compound of formula X in which $R^2$ is hydrogen may be prepared by reducing a compound of formula XI and where P in the compound of formula XI represents an amine protecting group, if necessary, subjecting the reduced compound obtained to deprotection. Alternatively where a compound of formula XI is used in which P represents an amine protecting group, the compound of formula XI may be subjected to deprotection prior to reduction.

Where it is desired to prepare a compound of formula X in which $R^2$ represents an alkyl group, the said compound may for example be prepared by reduction before or after alkylation or where alkylation is effected by reductive alkanoylation simultaneously with reduction. Alternatively where a compound of formula XI is used in which P represents an appropriate amine protecting group said compound may be reacted to convert the protecting group into the desired alkyl group.

Thus where it is desired to prepare a compound formula X in which $R^2$ is methyl, a compound of formula X in which $R^2$ is hydrogen may be subjected to methylation whereby to obtain the desired compound. Such a compound of formula X in which $R^2$ is methyl may also be prepared by reacting a compound of formula XI in which P represents an appropriate amine protecting group whereby to convert said amine protecting group into a methyl group. Such a reaction may for example be effected using a compound of formula XI in which P represents a benzyloxycarbonyl group, the reaction being effected by the use of a complex aluminium hydride reducing agent such as lithium aluminium hydride.

Where it is desired to prepare a compound of formula X in which $R^2$ is ethyl, n-propyl or isopropyl, a compound of formula X in which $R^2$ is hydrogen may be reacted with acetic or propionic acid or a reactive derivative thereof or with acetone, reduction being effected whereby to obtain the desired compound of formula X in which $R^2$ is ethyl, n-propyl or isopropyl.

The compound of formula XI may for example be prepared by reaction of a compound of formula XII (as set out hereinafter in which P and $Y^2$ are as hereinbefore defined) with a compound of formula XIII (as set out hereinafter in which $R^4$ and $R^5$ are as hereinbefore defined).

A compound of formula X may also be prepared by reduction of a compound of formula XIV in which $R^2$, $R^4$ and $R^5$ are as hereinbefore defined preferably using a complex aluminium hydride reducing agent such as lithium aluminium hydride. The compound of formula XIV is conveniently prepared by deprotecting a compound of formula XV (in which $P^1$ represents an amine protecting group and $R^2$, $R^4$ and $R^5$ are as hereinbefore defined), by methods known per se. The compound of formula XV may be prepared by reacting a compound of formula XVI (in which $R^1$, $R^2$ and Y are as hereinbefore defined) with a compound of formula XIII. The compound of formula XVI may be prepared by the amine protection of a compound of formula XVII.

The compounds corresponding to the compounds of the invention, but in which $R^3$ represents a phenyl group meta-substituted by hydroxy or amino and optionally further substituted as hereinbefore defined may also be prepared by the hydrolysis of a corresponding compound in which the said phenyl group is meta substituted by an acyloxy or acylamino group, or by the deprotection of a corresponding compound in which the said phenyl group is meta substituted by an alkoxy or benzyl group using, for example strong acid or boron tribromide.

If desired one compound of the present invention may be converted into another compound of the present invention by methods known per se.

Compounds of the invention and compounds corresponding to compounds of the invention but in which $R^3$ represents a phenyl group meta-substituted by hydroxy or amino and optionally further substituted as hereinbefore defined in which X represents a —SOCH$_2$— moiety, may be prepared by oxidising a corresponding compound of formulae II or III in which X represents an —SCH$_2$— or —SOCH$_2$-moiety.

Compounds of the invention and compounds corresponding to compounds of the invention but in which $R^3$ represents a phenyl group meta-substituted by hydroxy or amino and optionally further substituted as hereinbefore defined in which X represents an —SOCH$_2$— moiety, may be prepared by oxidising a corresponding compound of formula II or III in which X represents an —SCH$_2$— moiety.

The oxidation of —S— or —SO— to —SO$_2$ and the oxidation of —S— to —SO— is conveniently effected by methods known per se for example by the use of hydrogen peroxide advantageously in the presence of acetic acid or a haloacetic acid for example trifluoroacetic acid, or a peroxy acid, for example 3-chloroperbenzoic acid, advantageously in the presence of an appropriate chlorinated solvent, for example dichloromethane.

Where a 3-nitrophenylglycine is used as starting material the nitrophenyl moiety may if desired by reduced to the corresponding 3-aminophenyl moiety at any stage during the preparation of the compounds of the invention.

The compounds used as starting materials in the above-mentioned processes may contain radicals which are not compatible with at least certain of the processes described as will readily be appreciated by those skilled in the art and in such cases it is desirable to protect the starting material(s) by the use of an appropriate protecting group prior to the relevant reaction. After completion of the reaction the protecting group may if desired be removed or if desired may be left intact for removal after formation of the compound of formula I or racemate in protected form.

The relevant starting material may be in racemic form or in the desired optically active form. Where a racemate of the compound of formula I is obtained, the desired optically active enantiomer may be obtained by resolution according to conventional techniques. Where an optically active enantiomer of the compounds of formula I is obtained a racemate may if desired be obtained by racemisation according to conventional techniques.

Salts of the compounds of formula I or racemates thereof may if desired by prepared by reaction of the compound of formula I or racemate thereof with an appropriate acid, preferably an acid which affords a pharmaceutically acceptable anion for example a mineral acid such as hydrochloric acid or an organic acid such as fumaric or maleic acid.

Salts of the compound of formula I or racemate thereof may be converted to compounds of formula I or racemate thereof per se by conventional techniques, for example by ion exchange.

The compounds of the present invention are of interest in the treatment of medical conditions where stimulation of kappa receptors is appropriate, but where it is desired to avoid CNS (central nervous system) side effects. In particular compounds of the present invention possess hypotensive activity and certain compounds of the invention may possess an antiinflammatory activity.

The hypotensive activity of compounds of the invention has been demonstrated in the cardiovascular conscious dog test which was conducted as follows:

Conscious male beagle dogs (14–18 kgs), with previously implanted chronic indwelling arterial and venous catheters are used in this test. The animals are trained to lie quietly in a padded box. At the beginning of each experiment, control blood pressure, heart rate, E.C.G. and cardiac force measurements are taken. Aortic blood pressure is recorded via a pressure transducer and displayed on a direct writing oscillograph (MX4 or M19). Heart rate is electronically derived from the pulse pressure and displayed continuously. The ECG is derived via attached limb leads (lead II). Cardiac force measurements are made using the non-invasive technique of determination of the Q-A interval. After control measurements have been taken, the test substance is administered subcutaneously in a single dose. Subsequently at 2, 3 and 5 hours. In addition, any observable side effects will be noted.

The test substance was administered in a dose of 1.0 mg/kg dissolved in a small volume of 1% sodium bicarbonate and diluted with saline, the dose vehicle being 40% polyethylene alcohol/10% ethanol/40% saline and the dose volume being 5–10 mls.

Significant changes in blood pressure, when compared with control, were noted. Standard controls used were clonidine-250 µg/kg po and hydrallazine-10 mg/kg po.

The compounds of the present invention may also find use as a research tool and thus may be useful in the delineation of the role of peripheral, as opposed to central nervous system, kappa receptors.

According to a further feature of the present invention therefore we provide pharmaceutical compositions comprising as active ingredient at least one compound of formula I or racemate thereof or a pharmaceutically acceptable salt of said compound or racemate in association with a pharmaceutically acceptable carrier or diluent.

The pharmaceutical compositions of the invention may be in a form suitable for oral, parenteral, topical or rectal administration. Thus, for example, they may be in orally-administrable unit dosage form, for example tablets or capsules, which may optionally be adapted for sustained release, or in injectable form, for example a sterile injectable solution or suspension, or in the form of a suppository for rectal administration or in a topically administrable form for antiinflammatory indications, for example an ointment or a nasal spray. The said pharmaceutical compositions may be produced by conventional methods using conventional diluents or carriers.

The composition of the present invention may have veterinary as well as human applications, but where one of the compounds of the invention is used clinically in humans it is recommended to employ doses from 10 ug to 300 mg, for example 0.1 to 50 mg, once to four times per day, such a dosage range encompassing all routes of administration. No overt toxicity was noted at physiologically active doses.

According to a further feature of the present invention we provide a method of alleviating hypertension and/or inflammation in warm-blooded animals which comprises administering to such animals an effective amount of a compound of formula I or a racemate or pharmaceutically acceptable salt of said compound or racemate.

The invention is illustrated but not limited by the following Examples in which the temperatures are expressed in degrees Celsius:

EXAMPLE 1

2(R,S)-N-[2-(N-methyl-3,4-dichlorophenylacetamido)-2-(3-carboxymethoxyphenyl)-ethyl]pyrrolidine hydrochloride 2(R,S)-N-[2-(N-methyl-3,4-dichlorophenylacetamido)-2-(3-hydroxyphenyl)-ethyl]pyrrolidine (29.56 g), anhydrous potassium carbonate (32.28 g) and dry DMF (400 ml) were stirred under argon and treated with tert-butyl bromoacetate (9.2 ml). The mixture was stirred for 18 hours at ambient temperature and then diluted with water (2.5 l) and the product extracted with ethyl acetate (500 ml). The organic phase was washed with 3×100 ml brine, dried over magnesium sulphate and evaporated to a yellow oil which was purified by flash chromatography on silica using 2% tert butanol in dichloromethane giving 17.1 g pale yellow oil which was the tert butyl ester of the desired product.

10.22 g of the above ester were heated and stirred with 100 ml 6N HCl on a steam bath over 1¾ hours. The mixture was then cooled and the white product filtered off and dried over 18 hours under vacuum over phosphorus pentoxide. This product was recrystallised from acetonitrile (3700 ml) and dried at 60° under vacuum for 18 hours to give the product as fine white crystals. Melting point 207°–8°, yield 7.7 g.

2(R,S)-N-[2-(N-methyl-3,4-dichlorophenylacetamido)-2-(3-hydroxyphenyl)-ethyl]pyrrolidine used as starting material was obtained as follows:

a)

R,S-N-Benzyloxycarbonyl-2-(3-methoxyphenyl)glycine

R,S-2-(3-methoxyphenyl)glycine (21.72 g) was stirred in 120 ml 2N sodium hydroxide at 10° C. and 23.0 ml benzyl chloroformate added over ¼ hour. After stirring for a further 1 hour the mixture was washed with ether, acidified, and the resulting oil extracted with ether. This ether solution was washed with water, dried (MgSO$_4$) and evaporated to give 38.7 g of a pale yellow oil which crystallised on stirring with hexane. The pale cream crystals were collected, washed, and dried with 32.0 g (85%), M.Pt 97.0° C.

b)

R,S-N-Benzyloxycarbonyl-2-(3-methoxyphenyl)glycine, pyrrolidide 31.5 of R,S-2-(3-methoxyphenyl)glycine in 300 ml ethyl acetate was cooled in an ice/water bath and treated with 17.8 g carbonyldiimidazole. After stirring for 2 hours at 10°–15° C., 92 ml of pyrrolidine were added (mild exotherm). The mixture was stirred for 1 hour, washed three times with 2N HCl, once with saturated aq.NaHCO$_3$, and water, dried over MgSO$_4$ (+ decolourising charcoal), and evaporated to give 36.1 g (98%) of a very pale green oil.

Mass spectrum M/e 369 (M+H)$^+$, NMR (deuterochloroform): δ1.8 (4H,m), δ3.4 (4H,m), δ3.8 (3H,s), δ4.8 (2H,d), δ5.3 (1H,s), δ6.3 (1H,d) δ6.9 and 7.3 (9H,m).

c)
R,S-1-(3-methoxyphenyl)-1-methylamino-2-(1-pyrrolidino)ethane 11.4 g lithium tetrahydroaluminate was stirred in 500 ml dry THF under argon and 36.0 g R,S-N-Benzyloxycarbonyl-2-(3-methoxyphenyl)glycine, pyrrolidide was added over ½ hour at 10°–15° C. The mixture was stirred for ½ hour, and then heated 2 hours at 55° C. After cooling in ice the mixture was carefully quenched with excess saturated aqueous sodium carbonate solution, filtered, and evaporated to give 36 g colourless oil which was used without further purification.

d)
R,S-1-(3,4-dichloro-N-methylacetamido)-1-(3-methoxyphenyl)-2-(1-pyrrolidino)-ethane The above oil was dissolved in 250 ml dichloromethane and 26.8 g 3,4-dichlorophenylacetylchloride was added. After 10 minutes 600 ml ether were added and the mixture stood 18 hours at ambient temperature. The product (white crystals) was collected, washed with ether, and dried -wt 3.5 g (73% yield).

1.1 g of this product recrystallised from ethyl acetate containing a trace of methanol gave 850 mg pure product M.Pt 221°–2° C.

d)
R,S-1-(3,4-dichloro-N-methylacetamido)-1-(3-hydroxyphenyl)-2-(1-pyrrolidino)-ethane A solution of 44.0 g of the above methyl ether in 290 ml dichloromethane were stirred at −72° C. and 290 ml 1M. Boron tribromide in dichloromethane were added. The mixture was stirred for 1 hr at −70° C., warmed to ambient temperature and stirred for 6 hours. The mixture was carefully quenched at 0° C. with 500 ml methanol and the solution evaporated under reduced pressure. The resultant solid was stirred overnight with methanol/ether (200 ml and 300 ml) and filtered to give the product as a white solid (30.6 g) which was a mixture of the hydrochloride and hydrobromide salts of the products (this mixture being confirmed by acid/base filtration).

NMR (deutero DMSO+deuteroacetic acid) δ2.1 (4H,m), 2.7 (3H,s), δ3.1–4.2 (8H,m), δ6.1 (1H,9), δ6.7–7.5 (7H,m).

Mass spectrum (M+H)+ 407 under +ve FAB conditions.

3,4-Dichlorophenylacetyl chloride 3,4-Dichlorophenylacetic acid (76.8 g) was dissolved in dry dichloromethane (300 ml) and oxalyl chloride (52 g, 36 ml) was added to the solution obtained in one portion. The reaction mixture was protected from atmospheric moisture with a calcium chloride guard tube and stirred mechanically whilst dimethylformamide (3 drops) was added. The solution was stirred at ambient temperature for 18 hours and then evaporated under reduced pressure to give a yellow oil. Distillation in vacuo afforded 80.0 g of 3,4-dichlorophenylacetyle chloride, b.pt 97°–100°/0.6 mm, as a viscous pale yellow oil.

EXAMPLE 2
(R,S)-N-[2-(N-methyl-3,4-dichlorophenylacetamido)-2-(3-trimethylammoniumpropoxyphenyl)-ethyl]pyrrolidine iodide hydrochloride 1.0 g of (R,S)-N-[2-(N-methyl-3,4-dichlorophenylacetamido)-2-(3-dimethylaminopropoxyphenyl)ethyl]pyrrolidine in 5 ml acetone (analytical grade) was treated with 0.29 g iodomethane. After 72 hours at ambient temperature white crystals had separated and the mixture was filtered, the solid rejected, and the filtrate evaporated to give an oil which crystallised on stirring with ether. This (hygroscopic) solid was dried and recrystallised from acetone/ether (again rather hygroscopic). Stirred with ether and dried to give the product (500 mg) M.Pt 50°–3°.

The starting material (R,S)-N-[2-(N-methyl-3,4-dichlorophenylacetamido)-2-[3-dimethylaminopropoxy)-phenyl]-ethyl]pyrrolidine was obtained as follows:

3.46 g of (R,S)-N-[2-(N-methyl-3,4-dichlorophenylacetamido)-2-(3-hydroxyphenyl)-ethyl]pyrrolidine in 20 ml toluene were treated with 0.375 g of 55% sodium hydride in mineral oil (under Argon atmosphere) and the mixture stirred at 80°. 8.0 g Dimethylaminopropyl chloride hydrochloride were dissolved in 2 ml water and excess sodium hydroxide solution (10 molar) was added. The solution was extracted with 3×12 ml toluene and the extracts (not washed) dried over potassium hydroxide pellets and diluted to 50 ml with toluene. 25 ml of this solution were added over one hour to the phenoxide solution, and 10 mg sodium iodide added. The reaction was slow and so a further 25 ml of the halide solution was added and the reaction heated for 16 hours at 80°. After dilution with ethyl acetate the mixture was washed with water, dried over magnesium sulphate, and evaporated to give 5.0 g of pale yellow oil. This was dissolved in ether, treated with charcoal for a few minutes, filtered and treated with a solution of hydrogen chloride in ethyl acetate. The solid produced, which was in the form of a gum, was washed with ether and recrystallised from isopropanol to give 3.2 g of a white crystalline solid. 700 mg of this solid were recrystallised from ethyl acetate containing a few drops of methanol to give the pure dihydrochloride monohydrate of (R,S)-N-[2-(N-methyl-3,4-dichlorophenylacetamido)-2-(3-dimethylaminopropoxyphenyl) -ethyl]pyrrolidine m.p. 174°–5°.

The compound (R,S)-N-[2-(N-methyl-3,4-dichlorophenylacetamido)-2-(3-hydroxyphenyl)-ethyl]pyrrolidine used as starting material herein was obtained as described in Example 1.

EXAMPLE 3
(R,S)-N-[2-(N-methyl-3,4-dichlorophenylacetamido)-2-(3-benzyldimethylammoniumpropoxyphenyl)-ethylpyrrolidine chloride hydrochloride dihydrate This compound was made in an analogous manner to Example 2, using benzyl chloride in place of iodomethane. The product was not crystalline, evaporation of the acetone solution yielding a stable foam.

Analysis: Found: C, 61.2; H, 6.8; N, 6.3; Cl−, 5.1; Water, 5.1; Theory: C, 60.7; H, 6.8; N, 6.4; Cl−; 5/4; Water, 5.5.

NMR (deuterochloroform) δ1.75 (4H, broad s), δ2.2–2.6 (6H, m), δ2.7 (5H,t), δ2.9–3.4 (1H,m), δ3.35 (6H, s), δ3.75 (4H, m), δ4.0 (2H,m), δ5.0 (2H,s), δ6.0 (1H,q), δ6.7–7.7 (12H,m).

Mass spectrum m/e 582 (+me FAB conditions).

EXAMPLE 4

(R,S)-N-[2-(N-methyl-3,4-dichlorophenylacetamido)-2-(3-guanidinophenyl)-ethyl]pyrrolidine dihydrate (R,S)-N-[2-(N-methyl-3,4-dichlorophenylacetamido)-2-(3-aminophenyl)ethyl]pyrrolidine dihydrochloride hemihydrate (400 mg) and cyanamide (100 mg) were heated together in ethanol (10 ml) at reflux for 48 hours. During this time the ethanol was slowly allowed to evaporate off. The residue was chromatographed on silica 7734 (E. Merck) using $CHCl_3:MeOH:NH_3$ (60:40:5) parts by volume to give a white foam.

This was purified by preparative layer chromatography on 1.5 mm thick alumina prep.plates using 20% methanol/methylene chloride. The alumina/product sport was scraped of and extracted with methanol. This was evaporated and re-extracted into methylene chloride. ON filtration and evaporation the product was obtained as a white foam 86 mgs (18% yield).

Analysis: Found: C, 54.6; H, 6.1; N, 15.2; Water, 7.3; Theory: C, 54.5; H, 6.4; N, 14.5; Water, 7.4; for $C_{22}H_{27}N_5Cl0.2H_2O$ (484).

Mass spec. Molec. ion 448 (M+H)+

NMR. $H^1$NMR (DMSO $d_6$) 2.0 ppm. ($CH_2\times2$ 4H broad) 2.88 ($NCH_3$ 3H singlet) 3.0–3.22 ($CH_2N$ 2H broad) 3.45–4.1 ($CH_2N\times2$ 4H broad) 3.75–4.2 (ArCH$_2$CO 4H doublet of doublets) 6.12 CHAr (1H doublet of doublets) 7.1–7.7 (ArH broad multiplet).

The starting material (R,S)-N-[2-(N-methyl-3,4-dichlorophenylacetamido)-2-(3-aminophenyl)-ethyl]-pyrrolidine was obtained by follows:

(a)
(R,S)-N-[2-methoxycarbonylamino-2-(3-aminophenyl)acetyl]pyrrolidine

N-Methoxycarbonyl-(R,S)-3-nitrophenylglycine pyrrolidide (15.0 g) [prepared by protecting 3-nitrophenylglycine in conventional manner and subsequent reaction of protected compound with pyrrolidine in similar manner to that described in Example 1a] was dissolved in glacial acetic acid (200 ml). 3-nitrophenylglycine may be prepared by the method of Sriid and Kjaer, Acta. Chim. Scand. 1963, 17, page 2394.

The catalyst (10% Pd/C) (2.0 g) was added and the mixture was stirred at room temperature under a hydrogen atmosphere until uptake of the gas was complete. The hydrogen atmosphere was flushed away with argon and the mixture filtered through Celite to give a clear solution. This was evaporated and then azeotroped several times with toluene to remove the last traces of acetic acid to give an oil which slowly crystallised (14.5 g) m.p. 147°–9° (isopropanol).

(b) (R,S)-N-[2-methylamino-2-(3-aminophenyl)ethyl] pyrrolidine

The (R,S)-N-[2-methoxycarbonylamino-2-(3-aminophenyl)acetyl]pyrrolidine (5.0 g) was dissolved in dry tetrahydrofuran (100 ml) and added to a suspension of lithium aluminium hydride (2.0 g) in tetrahydrofuran (50 ml) with stirring whilst cooling in ice and under an argon atmosphere. After completion of the addition the mixture was stirred at reflux for 16 hours. After cooling to room temperature the excess lithium aluminum hydride was destroyed using saturated sodium carbonate solution, and the mixture was filtered and evaporated to leave an oil 3.5 g. This oil was columned using 30% methanol 70% methylene chloride and 0.1% aqueous ammonia (S.G. 0.88) on Merck silica 7734 to give an oil 2.7 g as the product (68% yield). Mass Spec. molecular ion at 220 (M+H)+ NMR: $H^1$ NMR ($CD_3CO_2D$) 2.0 ppm ($CH_2\times2$ 4H broad) 2.55 ($NCH_3$ 3H singlet) 3.35–4.4 (one $CH_2$ masked by water from the $CD_3CO_2D$) ($CH_2N\times3$ 6H multiplet) 4.75 (CH 1H triplet) 6.85–7.5 (CH aromatic$\times4$ 4H multiplet).

(c)
(R,S)-N-[2-(N-methyl-3,4-dichlorophenylacetamido)-2-(3,4-dichlorophenylacetamido)-phenyl-ethyl]pyrrolidine (R,S)-N-[2-methoylamino-2-(3-aminophenyl)acetyl]-pyrrolidine (14.3 g) was dissolved in dichloromethane (1200 ml) and 3,4-dichlorophenylacetyl chloride (29.2 g) was added slowly with ice cooling to the stirred solution. After completion of the addition the mixture was stirred for 3 hours at room temperature. The solvent was evaporated and the residue was triturated with ether and filtrated to give an off white solid 34.0 g m.p. 249°–251° (methanol/ethyl acetate).

(d)
(R,S)-N-[2-(N-Methyl-3,4-dichlorophenylacetamido)-2-(3-aminophenyl)ethyl]pyrrolidine hydrochloride (R,S)-N-[2-(N-Methyl-3,4-dichlorophenylacetamido)-2-(3,4-dichlorophenylacetamidophenyl)ethyl] pyrrolidine (34 g) was refluxed in 20:80 water:ethanol (by volume) (200 ml) containing sodium hydroxide pellets (20 g) overnight. The mixture was evaporated under reduced pressure to remove most of the ethanol and then extracted with ethyl acetate. The organic layer was washed with water and then brine and finally dried ($MgSO_4$) and evaporated to give an oil, yield: 21.0 g.

A sample with ethereal hydrogen chloride gave a white solid (dihydrochloride) m.p. 248°–9° (methanol/ethyl acetate).

The Octan-1-ol-water distribution coefficient referred to hereinbefore may be determined as follows:

The compound for test is dissolved (1 mg/50 ml) buffer (0.01M Phosphate, pH 7.4) presaturated with the organic solvent. The u.v. spectrum is recorded to ensure that the u.v. absorbance is between 0.3 and 1.5 units for at least one band in the spectrum, preferably at $\lambda>250$ nm. The solution is filtered to remove excess solid material and transferred (5 ml) by pipette into a stoppered test tube. The required volume of octan-1-ol, presaturated with water at the appropriate pH, is then transferred, again by pipette into the test tube. Ideally the ratio of aqueous to organic should be such that an absorbance change of fifty percent is achieved, although a minimum aqueous volume of 3 ml is required. The stoppered test tube is then vigorously shaken for several minutes and allowed to stand for fifteen minutes. The mixture is transferred by pipette into a centrifuge tube and placed in the centrifuge opposite a second tube containing an equal volume of water and spun at 3600 r.p.m. for ten minutes. The centrifuge tube is removed and the upper layer is carefully removed by pasteur pipette. A second centrifugation may be necessary after this process to reseparate the layers. Using a second, clean pasteur pipette placed to the bottom of the centrifuge tube with application of positive pressure, the aqueous layer (2–3 ml) is transferred to the cuvette taking care not to carry over droplets of the organic layer. The u.v. spectrum of this solution is taken overlaid onto the u.v. spectrum of the starting aqueous stock solution, both referenced against aqueous buffer. The spectrum of the stock solution should be compared with the original spectrum to ensure no degradation of the compound has occurred during the experiment.

The distribution coefficient, D, is calculated using the following equation $$D = \frac{A_{B,w} - A_{A,w}}{A_{A,w}} \times \frac{V_w}{V_o}$$

$A_{B,w}$ = Absorbance in aqueous phase before addition of organic layer
$A_{A,w}$ = Absorbance in aqueous phase after addition of organic layer
$V_w$ = Volume of the aqueous phase
$V_o$ = Volume of the aqueous phase The result must be the same whatever the wavelength chosen. In all cases the measurement is confirmed by repeating the experiment by partitioning from the organic solvent into water. The result of the reverse experiment can be calculated by the following expression $$D = \frac{A_{A,o}}{A_{B,o} - A_{A,o}} \times \frac{V_w}{V_o}$$

$A_{A,o}$ = Absorbance in organic phase before addition of buffer
$A_{B,o}$ = Absorbance in organic phase after addition of buffer Pharmaceutical Composition Examples Example A

| Tablets: | |
|---|---|
| Each tablet contains: | |
| 2(RS)-N-[2-(N-methyl-3,4-dichlorophenylacetamido)-2-(3-carboxymethoxyphenyl-ethyl]pyrrolidine hydrochloride | 0.1 mg |
| Dicalcium phosphate | 42 mg |
| Methylcellulose, U.S.P. (15 c.p.s) | 1.6 mg |
| Lactose | 6 mg |
| Calcium Stearate | 0.5 mg |

The active ingredient and dicalcium phosphate are mixed well, granulated with a 7.5% aqueous solution of methylcellulose, passed through a No. 8 screen and dried. The granulate obtained is then passed through a No. 12 screen, mixed with the remaining ingredients (lactose and calcium stearate) and compressed to yield tablets each weighing approximately 50 mg.

Example B

| Capsules: | |
|---|---|
| Each capsule contains: | |
| Compound of the present invention | 0.2 mg |
| Lactose U.S.P. | 47 mg |
| Starch U.S.P | 2.5 mg |
| Calcium stearate | 0.35 mg |

The above-mentioned ingredients are obtained in finely powdered form, mixed thoroughly and then filled into appropriately sized hard gelatin capsules.

I claim:
1. A compound of formula I

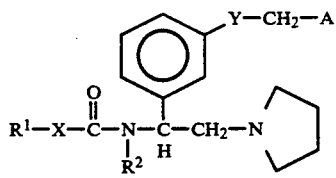

wherein:
$R^1$ represents a halophenyl, dihalophenyl, nitrophenyl, cyanophenyl or trifluoromethylphenyl group;
X represents a single bond, —$CH_2$—, —$OCH_2$—, —$SCH_2$—, —$S(O)CH_2$—, —$S(O)_2(CH_2$— or —$CH_2$—$CH_2$—;
$R^2$ represents hydrogen or $C_{1-3}$alkyl;
Y represents a single bond, —S—, —O—, or —N(R)— in which R represents hydrogen methyl, formyl or acetyl; and
A represents —COOH or —$SO_3H$; or racemate thereof, or a salt of said compound of formula I or racemate thereof; the groups Y and A being selected such that the compound of formula I or racemate thereof or salt of said compound of formula I or racemate thereof has a log D of less than 0.5 at pH 7.4, where log D is the logarithm of the distribution coefficient between octan-1-ol and aqueous buffer.

2. The compound as claimed in claim 1 wherein $R^1$ represents chlorophenyl, dichlorophenyl, bromophenyl, fluorophenyl, difluorophenyl, trifluoromethylphenyl, nitrophenyl or cyanophenyl.

3. The compound as claimed in claim 2 wherein $R^1$ represents 3-chlorophenyl, 4-chlorophenyl, 3,4-dichlorophenyl, 4-bromophenyl, 3-fluorophenyl, 4-fluorophenyl, 3,4-dichlorophenyl, 4-(trifluoromethyl)-phenyl, 4-nitrophenyl or 4-cyanophenyl.

4. The compound as claimed in claim 1 wherein X is —$CH_2$—, —$OCH_2$—, —$SCH_2$— or —$CH_2CH_2$—.

5. The compound as claimed in claim 1 wherein $R^2$ is methyl.

6. The compound as claimed in claim 1 wherein when Y represents —N(R)—, R is hydrogen.

7. The compound as claimed in claim 1 wherein Y is —O— and A is —COOH.

8. The compound 2(R,S)-N-[2-(N-methyl-3,4-dichlorophenylacetamido)-2-(3-carboxymethoxyphenyl)ethyl]pyrrolidine or salt thereof.

9. A pharmaceutical composition comprising as active ingredient a therapeutically effective amount of at least one compound of formula I as claimed in claim 1 or racemate thereof or pharmaceutically acceptable salt of said compound of formula I or racemate thereof, in association with a pharmaceutically acceptable carrier or diluent.

10. A method of alleviating hypertension or inflammation in a warm-blooded animal which comprises administering to said animal a therapeutically effective amount of a compound of formula I as claimed in claim 1 or racemate thereof or pharmaceutically acceptable salt of said compound of formula I or racemate thereof.

* * * * *